United States Patent [19]
Kunstmann et al.

[11] 3,980,656
[45] Sept. 14, 1976

[54] PARTIALLY HYDROGENATED 1H-INDENO[1,2-b]-PYRIDINE DERIVATIVES

[75] Inventors: Rudolf Kunstmann, Hofheim, Taunus; Ernold Granzer, Kelkheim, Taunus, both of Germany

[73] Assignee: Hoechst Aktiengesellschaft, Frankfurt am Main, Germany

[22] Filed: May 16, 1974

[21] Appl. No.: 470,667

[30] Foreign Application Priority Data
May 19, 1973 Germany.......................... 2325581

[52] U.S. Cl..................... 260/293.54; 260/294.8 T; 260/295 L; 260/297 Z; 260/465 F; 260/471 R; 260/518 R; 424/267
[51] Int. Cl.².................................. C07D 221/16
[58] Field of Search........................... 260/293.54

[56] References Cited
UNITED STATES PATENTS

| | | | |
|---|---|---|---|
| 2,470,109 | 5/1949 | Plati et al............................ | 260/290 |
| 3,839,338 | 10/1974 | Albertson et al. .............. | 260/287 R |

*Primary Examiner*—G. Thomas Todd
*Attorney, Agent, or Firm*—Curtis, Morris & Safford

[57] ABSTRACT

Partially hydrogenated 1H-indeno[1,2-b]-pyridine derivatives of the general formula I

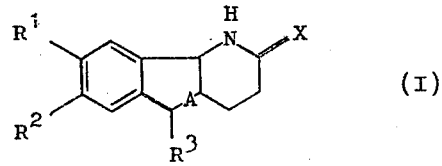

(I)

in which
  $R^1$ and $R^2$, which may be identical or different, represent hydrogen, halogen or alkoxy of 1 to 4 carbon atoms,
  $R^3$ represents pyridyl, phenyl, or phenyl mono- or di-substituted by halogen, nitro, amino, acylamino, alkyl having 1 to 4 carbon atoms, alkoxy having 1 to 4 carbon atoms, or amino substituted by 1 or 2 aliphatic or aromatic hydrocarbon groups having 2 to 18 carbon atoms or substituted amino wherein the amino-nitrogen is included in a heterocycle,
  A represents a single or double bond, and
  X represents oxygen or sulfur, and their physiologically tolerated salts, process for preparing them and pharmaceutical preparations containing them.

9 Claims, No Drawings

PARTIALLY HYDROGENATED 1H-INDENO[1,2-b]-PYRIDINE DERIVATIVES

The present invention relates to partially hydrogenated 1H-indeno[1,2-b]-pyridine derivatives of the general formula I

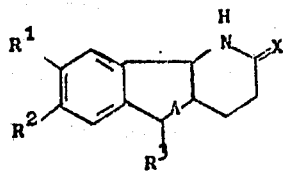

in which
R$^1$ and R$^2$, which may be identical or different, represent hydrogen, halogen or alkoxy of 1 to 4 carbon atoms,
R$^3$ represents phenyl which may be mono- or di-substituted by halogen, nitro, amino groups or an amino group which may be substituted by 1 or 2 aliphatic or aromatic hydrocarbon radicals of 2 to 18 carbon atoms, in which the nitrogen atom may also be included in a heterocycle, an acylamino group, an alkyl or alkoxy group each having 1 to 4 carbon atoms, or the pyridyl radical,
A represents a single or double bond, and
X represents oxygen or sulfur,
and to their physiologically tolerated salts.

In particular, the present invention relates to compounds in which R$^1$ and R$^2$ are identical and represent hydrogen or the methoxy group, or R$^1$ represents hydrogen and R$^2$ represents chlorine or the methoxy group. As regards the substituent R$^3$, there may be used in particular the pyridyl radical, the phenyl radical, and a phenyl radical which may be substituted by methoxy, one or two chlorine atoms, or a nitro or amino group, or a combination of one chlorine atom and a nitro or amino group. Among the acylamino radicals, aliphatic radicals of 1 to 4 carbon atoms or aromatic radicals of 7 to 9 carbon atoms are preferred.

The present invention furthermore relates to a process for preparing the above-specified compounds and to pharmaceutical preparations of said compounds.

The processes for preparing the compounds of the invention are characterized in that
a. compounds of the general formula II

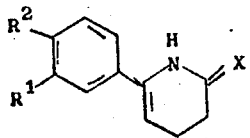

are reacted with an aldehyde of the general formula III

R$_3$ — CHO      III to yield compounds of the general formula I

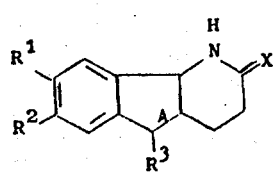

in which A represents a double bond,
b. compounds of the general formula IV

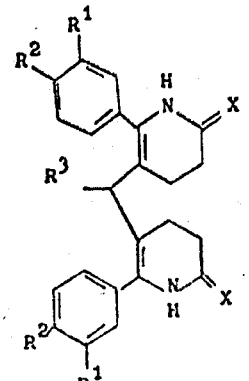

are cyclized, with separation of a 6-phenyl-3,4-dihydro-pyridine-2-one or -2-thione, to compounds of the formula I (A = double bond),
c. compounds of the general formula V

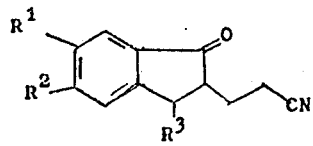

are cyclized to compounds of the general formula I (X = O, A = double bond),
d. compounds of the general formula VI

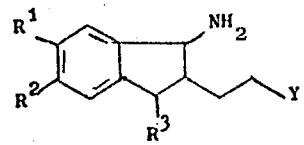

in which
Y represents a carboxylic acid radical or a reactive derivative thereof are cyclized to compounds of the general formula I (A = single bond),
and in the reaction products, if desired or required,
the double bond is hydrogenated in known manner,
the oxygen in compounds of the formula I (X = oxygen, A = single or double bond) is, if desired or required, replaced by sulfur in known manner, or
the sulfur of the compounds of the formula I (X = sulfur, A = single or double bond) is, if desired or required, replaced by oxygen in known manner.

The compounds of the general formula II (X = O) may be obtained in known manner [for example according to Zhur. Obshchei. Khim. 30, 1762 (1960)] from the correspondingly substituted γ-benzoylbutyric acid nitriles VII by cyclization the starting compounds of the general formula VII being prepared in the usual manner. For the exchange of the oxygen, by sulfur to form compounds of the formula II (X = S), the usually employed methods are used.

The compounds so obtained of the general formula II are reacted in the presence of acid catalysts, with or without solvent, with an aldehyde (III). In this smooth reaction, there are formed the compounds of the formula I (A = double bond). As catalysts, mineral acids such as sulfuric acid, hydrochloric acid and phosphoric acid, Lewis acids such as boron trifluoride and aluminium chloride, as well as phosphorusoxychloride are particularly suitable. As solvents, for example benzene, toluene, carbon tetrachloride or trichloroethylene may be used. The most simple method consists in reacting both reaction partners in phosphoric acid, the phosphorus pentoxide content of which may vary between that of 85% phosphoric acid and that of polyphosphoric acid. The operation is carried out at temperatures in the range of from 20° to 150° C, a temperature range of from 60° to 90° C being preferred. The phosphoric acid preferred for the reaction is prepared in the simplest way by combining 30 to 70 ml of 85% phosphoric acid with 30 to 70 g of phosphorus pentoxide. The mixing proportion which is the most suitable for the reaction is at 1 milliliter of 85% phosphoric acid per gram of phosphorus pentoxide. The reaction time is in the range of from about 15 minutes to 10 hours.

The compounds of the formula I (X = O, A = double bond) may also be prepared by directly reacting, without isolation of the compounds II, the compounds VII under the above reactions conditions with the aldehyde in a one-pot process.

The starting compounds IV, which are used in method (b), may be obtained, for example, by reacting 2 moles of the compounds II with 1 mole of the aldehyde III. This can be carried out, for example, by reacting both reaction partners, with or without the addition of an acid catalyst, and with or without solvent. Direct reaction of the reaction partners at elevated temperature or reaction in an inert solvent, for example benzene with addition of catalytic amounts of acid, for example p-toluene-sulfonic acid, is the most suitable.

Cyclization of the compounds IV to compounds of the formula I (X = O, A = double bond) can be carried out analogously to the conditions indicated for method (a).

The starting compounds V for the process (c) are obtained in the conventional manner from the indanones VIII by cyanoethylation (for example, J. Chem. Soc. (C) (1956), 959).

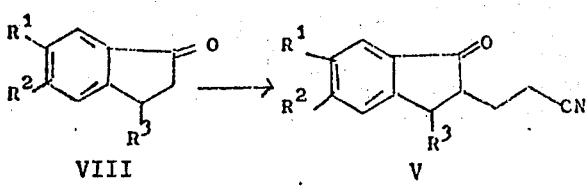

VIII   V

The compounds VIII are synthetized in known manner. Cyclization of the compounds V to compounds of the formula I (X = O, A = double bond) can be carried out analogously to the conditions indicated for method a).

The starting compounds VI for method d) may be obtained in known manner from compounds of the general formula V.

The compounds of the invention corresponding to the general formula I have hitherto not yet been described and therefore are novel compounds.

In addition to the compounds described in the Examples, there may also be prepared as compounds of the invention, preferably the following compounds:

5-(2',4'-dichlorophenyl)-2,3,4,9b-tetrahydro-1H-indeno-[1,2-b]-pyridine-2-one
5-(3',4'-dichlorophenyl)-2,3,4,9b-tetrahydro-1H-indeno-[1,2-b]-pyridine-2-one
5-(4'-chloro-3'-nitrophenyl)-2,3,4,9b-tetrahydro-1H-indeno-[1,2-b]-pyridine-2-one
5-(3'-chloro-4'-nitrophenyl)-2,3,4,9b-tetrahydro-1H-indeno-[1,2-b]-pyridine-2-one
5-(4'-chloro-3'-aminophenyl)-2,3,4,9b-tetrahydro-1H-indeno-[1,2-b]-pyridine-2-one
5-(3'-chloro-4'-aminophenyl)-2,3,4,9b-tetrahydro-1H-indeno-[1,2-b]-pyridine-2-one
5-(2',4'-dichlorophenyl)-7-chloro-2,3,4,9b-tetrahydro-1H-indeno-[1,2-b]-pyridine-2-one
5-(3',4'-dichlorophenyl)-7-chloro-2,3,4,9b-tetrahydro-1H-indeno-[1,2-b]-pyridine-2-one
5-(4'-chloro-3'-nitrophenyl)-7-chloro-2,3,4,9b-tetrahydro-1H-indeno-[1,2-b]-pyridine-2-one
5-(3'-chloro-4'-nitrophenyl)-7-chloro-2,3,4,9b-tetrahydro-1H-indeno-[1,2-b]-pyridine-2-one
5-(4'-chloro-3'-aminophenyl)-7-chloro-2,3,4,9b-tetrahydro-1H-indeno-[1,2-b]-pyridine-2-one
5-(3'-chloro-4'-aminophenyl)-7-chloro-2,3,4,9b-tetrahydro-1H-indeno[1,2-b]-pyridine-2-one
5-(2',4'-dichlorophenyl)-7,8-dimethoxy-2,3,4,9b-tetrahydro-1H-indeno[1,2-b]-pyridine-2-one
5-(3',4'-dichlorophenyl)-7,8-dimethoxy-2,3,4,9b-tetrahydro-1H-indeno-[1,2-b]-pyridine-2-one
5-(4'-chloro-3'-nitrophenyl)-7,8-dimethoxy-2,3,4,9b-tetrahydro-1H-indeno-[1,2-b]-pyridine-2-one
5-(3'-chloro-4'-nitrophenyl)-7,8-dimethoxy-2,3,4,9b-tetrahydro-1H-indeno-[1,2-b]-pyridine-2-one
5-(4'-chloro-3'-aminophenyl)-7,8-dimethoxy-2,3,4,9b-tetrahydro-1H-indeno-[1,2-b]-pyridine-2-one
5-(3'-chloro-4'-aminophenyl)-7,8-dimethoxy-2,3,4,9b-tetrahydro-1H-indeno-[1,2-b]-pyridine-2-one 5-(2',4'-dichlorophenyl)-2,3,4,9b-tetrahydro-1H-indeno [1,2-b] pyridine-2-thione
5-(3',4'-dichlorophenyl)-2,3,4,9b-tetrahydro-1H-indeno [1,2-b] pyridine-2-thione
5-(4'-chloro-3'-nitrophenyl)-2,3,4,9b-tetrahydro-1H-indeno-[1,2-b]-pyridine-2-thione
5-(3'-chloro-4'-nitrophenyl)-2,3,4,9b-tetrahydro-1H-indeno-[1,2-b]-pyridine-2-thione
5-(4'-chloro-3'-aminophenyl)-2,3,4,9b-tetrahydro-1H-indeno-[1,2-b]-pyridine-2-thione
5-(3'-chloro-4'-aminophenyl)-2,3,4,9b-tetrahydro-1H-indeno-[1,2-b]-pyridine-2-thione
5-(2',4'-dichlorophenyl)-7-chloro-2,3,4,9b-tetrahydro-1H-indeno-[1,2-b]-pyridine-2-thione
5-(3',4'-dichlorophenyl)-7-chloro-2,3,4,9b-tetrahydro-1H-indeno-[1,2-b]-pyridine-2-thione
5-(4'-chloro-3'-nitrophenyl)-7-chloro-2,3,4,9b-tetrahydro-1H-indeno-[1,2-b]-pyridine-2-thione
5-(3'-chloro-4'-nitrophenyl)-7-chloro-2,3,4,9b-tetrahydro-1H-indeno-[1,2-b]-pyridine-2-thione 5-(4'-chloro-3'-aminophenyl)-7-chloro-2,3,4,9b-tetrahydro-1H-indeno-[1,2-b]-pyridine-2-thione
5-(3'-chloro-4'-aminophenyl)-7-chloro-2,3,4,9b-tetrahydro-1H-indeno-[1,2-b]-pyridine-2-thione
5-(2',4'-dichlorophenyl)-7,8-dimethoxy-2,3,4,9b-tetrahydro-1H-indeno-[1,2-b]-pyridine-2-thione
5-(3',4'-dichlorophenyl)-7,8-dimethoxy-2,3,4,9b-tetrahydro-1H-indeno-[1,2-b]-pyridine-2-thione
5-(4'-chloro-3'-nitrophenyl)-7,8-dimethoxy-2,3,4,9b-tetrahydro-1H-indeno-[1,2-b]-pyridine-2-thione
5-(3'-chloro-4'-nitrophenyl)-7,8-dimethoxy-2,3,4,9b-tetrahydro-1H-indeno-[1,2-b]-pyridine-2-thione
5-(4'-chloro-3'-aminophenyl)-7,8-dimethoxy-2,3,4,9b-tetrahydro-1H-indeno-[1,2-b]-pyridine-2-thione
5-(3'-chloro-4'-aminophenyl)-7,8-dimethoxy-2,3,4,9b-tetrahydro-1H-indeno-[1,2-b]-pyridine-2-thione 5-(2',4'-dichlorophenyl)-2,3,4,4a,5,9b-hexahydro-1H-indeno-[1,2-b]-pyridine-2-one
5-(3',4'-dichlorophenyl)-2,3,4,4a,5,9b-hexahydro-1H-indeno-[1,2-b]-pyridine-2-one
5-(4'-chloro-3'-nitrophenyl)-2,3,4,4a,5,9b-hexahydro-1H-indeno[1,2-b]-pyridine-2-one
5-(3'-chloro-4'-nitrophenyl)-2,3,4,4a,5,9b-hexahydro-1H-indeno[1,2-b]-pyridine-2-one
5-(4'-chloro-3'-aminophenyl)-2,3,4,4a,5,9b-hexahydro-1H-indeno-[1,2-b]-pyridine-2-one
5-(3'-chloro-4'-aminophenyl)-2,3,4,4a,5,9b-hexahydro-1H-indeno-[1,2-b]-pyridine-2-one
5-(2',4'-dichlorophenyl)-7-chloro-2,3,4,4a,5,9b-hexahydro-1H-indeno-[1,2-b]-pyridine-2-one
5-(3',4'-dichlorophenyl)-7-chloro-2,3,4,4a,5,9b-hexahydro-1H-indeno-[1,2-b]-pyridine-2-one
5-(4'-chloro-3'-nitrophenyl)-7-chloro-2,3,4,4a,5,9b-hexahydro-1H-indeno-[1,2-b]-pyridine-2-one
5-(3'-chloro-4'-nitrophenyl)-7-chloro-2,3,4,4a,5,9b-hexahydro-1H-indeno-[1,2-b]-pyridine-2-one
5-(4'-chloro-3'-aminophenyl)-7-chloro-2,3,4,4a,5,9b-hexahydro-1H-indeno-[1,2-b]-pyridine-2-one
5-(3'-chloro-4'-aminophenyl)-7-chloro-2,3,4,4a,5,9b-hexahydro-1H-indeno-[1,2-b]-pyridine-2-one
5-(2',4'-dichlorophenyl)-7,8-dimethoxy-2,3,4,4a,5,9b-hexahydro-1H-indeno-[1,2-b]-pyridine-2-one
5-(3',4'-dichlorophenyl)-7,8-dimethoxy-2,3,4,4a,5,9b-hexahydro-1H-indeno-[1,2-b]-pyridine-2-one
5-(4'-chloro-3'-nitrophenyl)-7,8-dimethoxy-2,3,4,4a,5,9b-hexahydro-1H-indeno-[1,2-b]-pyridine-2-one
5-(3'-chloro-4'-nitrophenyl)-7,8-dimethoxy-2,3,4,4a,5,9b-hexahydro-1H-indeno-[1,2-b]-pyridine-2-one
5-(4'-chloro-3'-aminophenyl)-7,8-dimethoxy-2,3,4,4a,5,9b-hexahydro-1H-indeno-[1,2-b]-pyridine-2-one
5-(3'-chloro-4'-aminophenyl)-7,8-dimethoxy-2,3,4,4a,5,9b-hexahydro-1-H-indeno-[1,2-b]-pyridine-2-one 5-(2',4'-dichlorophenyl)-2,3,4,4a,5,9b-hexahydro-1H-indeno-[1,2-b]-pyridine-2-thione
5-(3',4'-dichlorophenyl)-2,3,4,4a,5,9b-hexahydro-1H-indeno-[1,2-b]-pyridine-2-thione
5-(4'-chloro-3'-nitrophenyl)-2,3,4,4a,5,9b-hexahydro-1H-indeno-[1,2-b]-pyridine-2-thione
5-(3'-chloro-4'-nitrophenyl)-2,3,4,4a,5,9b-hexahydro-1H-indeno-[1,2-b]-pyridine-2-thione
5-(4'-chloro-3'-aminophenyl)-2,3,4,4a,5,9b-hexahydro-1H-indeno-[1,2-b]-pyridine-2-thione
5-(3'-chloro-4'-aminophenyl)-2,3,4,4a,5,9b-hexahydro-1H-indeno-[1,2-b]-pyridine-2-thione
5-(2',4'-dichlorophenyl)-7-chloro-2,3,4,4a,5,9b-hexahydro-1H-indeno-[1,2-b]-pyridine-2-thione
5-(3',4'-dichlorophenyl)-7-chloro-2,3,4,4a,5,9b-hexahydro-1H-indeno-[1,2-b]-pyridine-2-thione
5-(4'-chloro-3'-nitrophenyl)-7-chloro-2,3,4,4a,5,9b-hexahydro-1H-indeno-[1,2-b]-pyridine-2-thione
5-(3'-chloro-4'-nitrophenyl)-7-chloro-2,3,4,4a,5,9b-hexahydro-1H-indeno-[1,2-b]-pyridine-2-thione
5-(4'-chloro-3'-aminophenyl)-7-chloro-2,3,4,4a,5,9b-hexahydro-1H-indeno-[1,2-b]-pyridine-2-thione
5-(3'-chloro-4'-aminophenyl)-7-chloro-2,3,4,4a,5,9b-hexahydro-1H-indeno-[1,2-b]-pyridine-2-thione
5-(2',4'-dichlorophenyl)-7,8-dimethoxy-2,3,4,4a,5,9b-hexahydro-1H-indeno-[1,2-b]-pyridine-2-thione
5-(3',4'-dichlorophenyl)-7,8-dimethoxy-2,3,4,4a,5,9b-hexahydro-1H-indeno-[1,2-b]-pyridine-2-thione
5-(4'-chloro-3'-nitrophenyl)-7,8-dimethoxy-2,3,4,4a,5,9b-hexahydro-1H-indeno-[1,2-b]-pyridine-2-thione
5-(3'-chloro-4'-nitrophenyl)-7,8-dimethoxy-2,3,4,4a,5,9b-hexahydro-1H-indeno-[1,2-b]-pyridine-2-thione
5-(4'-chloro-3'-aminophenyl)-7,8-dimethoxy-2,3,4,4a,5,9b-hexahydro-1H-indeno-[1,2-b]-pyridine-2-thione
5-(3'-chloro-4'-aminophenyl)-7,8-dimethoxy-2,3,4,4a,5,9b-hexahydro-1H-indeno-[1,2-b]-pyridine-2-thione The compounds of the general formula I (A = single bond) contain three asymmetrical carbon atoms. This means that, when preparing the compounds of the invention according to method (d), 8 stereo-isomeric compounds result. Thus the invention covers all compounds of the general formula I, independently of the steric arrangement of the 4a, 5 or 9b carbon atom.

Upon hydrogenation of the compounds of the general formula I (A = double bond) to compounds I (A = single bond), the cis-$H_{4a}H_5$, cis-$H_{9b}H_{4a}$ compounds are formed. The compounds having an all-cis arrangement in the pentagonal ring of the indane structure may be isomerized in an alkaline medium, for example with KOH in butanol to the corresponding trans-$H_{4a}H_5$, cis-$H_{9b}H_{4a}$ compounds. The amino-acids IX resulting intermediarily after the reaction with alkali are cyclized according to the usual methods again to lactams.

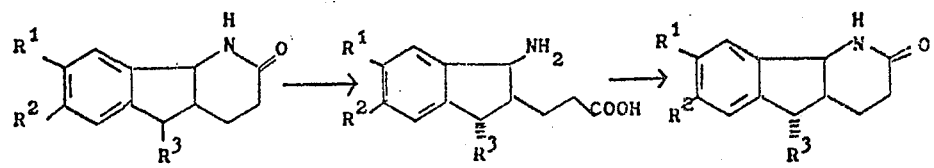

I    IX    X

The conversion of the free compounds into physiologically tolerated salts is effected according to known methods. As salts, there may be used, for example the hydrochloride, sulfate, phosphate, lactate and citrate.

The compounds of the invention have valuable therapeutic properties. They lower serum lipids, in particular the triglycerides, and may therefore be used for the therapy of primary hyperlipidemias and certain hyperlipidemias, for example in the case of diabetes in which they exert a favorable effect on a disturbed diabetic metabolism.

Since hyperlipidemia is the most dangerous cause of coronary heart diseases and, generally speaking, elevated serum lipid levels involve a great risk of causing arteriosclerotic diseases also of different localization and not only of the coronary vessels, the reduction of elevated serum lipid levels is extremely important for the prevention and therapy of arteriosclerosis, especially of the coronary heart vessels. Capable of reducing normal and elevated serum lipid levels in animals, the above-specified substances are useful for the treatment and prevention of arteriosclerotic diseases, especially of the coronary vessels but also of other blood vessels.

The hypolipidemic activity of the cited compounds could, inter alia, be demonstrated by the following tests:

1. Male rats having a normal serum lipid content were treated for eight days with different daily doses mentioned in Table 1. The values given in that Table stand for a change in the serum concentration of certain lipid classes. The compounds were administered per os by means of an esophagal sound. Generally, prior to and after the treatment, blood samples were taken and the concentration of cholesterol in the serum was determined according to the method of Lauber and Richterich and that of triglycerides according to the method of Eggstein and Kreutz. In the examples cited in the following Tables, the changes in the serum lipid levels due to the treatment with the substances are defined as follows:
   a. The changes in percent in the final value of the treated group, referred to the initial value of the treated group, the initial value being defined as 100 percent, and
   b. the change in the final value of the treated group, referred to the final value of an accompanying untreated control group (placebo group), the placebo group's value being defined as 100 percent. Thus, the value given in columns A is the change in percentage compared to the initial value, the value given in columns B is the change in percentage of the treated group, referred to that of the placebo group.

2. The hypertriglyceridemia induced by carbohydrates and initiated by fructose doses in male rats is substantially reduced by a 3-day oral pretreatment with the cited substances in comparison to a placebo group (see Table 2).

The novel compounds may be administered either as such or in admixture with pharmacologically acceptable carriers, an oral dosage unit form being preferred. For this purpose, the active substances are mixed with known substances and brought into suitable dosage unit forms according to methods known per se, for example into tablets, hard gelatine capsules, aqueous or oily suspensions or aqueous or oily solutions. As inert carriers, there may be used, for example, magnesium carbonate, lactose or corn starch with the addition of other substances, for example magnesium stearate. The compositions may be obtained by dry or moist granulation. Oily carriers or solvents are, in particular, vegetable and animal oils, for example sunflower oil or cod-liver oil. The daily dosage is about 0.5 to 4 g, preferably distributed to several single doses. A dosage unit contains preferably 250 to 500 mg of a compound of the invention.

A specific utility of the novel compounds is that they can be combined with other active substances. In addition to other suitable substances, there may be mentioned, above all, antidiabetics, as for example glycodiazin, tolbutamide, glibenclamide, phenformin, buformin, metformin, or agents acting on the circulatory system in their widest meaning, especially those dilating the coronary vessels, such as chromonar or prenylamine, and hypotensive substances, such as Reserpin, α-methyl-dopa or clonidine, further hypolipemic agents or geriatrics, psycho-pharmaceutics, for example chloro-diazepoxide, diazepam or meprobamate, as well as vitamins.

TABLE 1

| | % change after 8 peroral administrations of mg/kg/day to the male rat | | | | | |
|---|---|---|---|---|---|---|
| | 100 | | 30 | | 10 | |
| compound from example | serum cholesterol | serum triglycerides | serum cholesterol | serum triglycerides | serum cholesterol | serum triglycerides |
| | A/B | A/B | A/B | A/B | A/B | A/B |
| 1 | | | −13/ | −37/−21 | −17/−11 | |
| 3 | | | −4/−19 | −5/−23 | | −7/−22 |
| 7 | −19/−21 | −70/−70 | | | −10/−16 | −47/−27 |
| 8 | | | | −15/−13 | | |
| 9 | −13/−19 | −37/−19 | | | | −12/−20 |
| 10 | −15/−14 | −25/−38 | | −37/−30 | | −11/−18 |
| 11 | | | −2/−14 | /−37 | | |
| 16 | −28/−5 | −36/−44 | | | | |
| 17 | −6/−11 | −22 | | | | |
| 18 | | −48/−37 | | | | −24/−7 |

TABLE 1-continued

| | % change after 8 peroral administrations of mg/kg/day to the male rat | | | | | |
|---|---|---|---|---|---|---|
| | 100 | | 30 | | 10 | |
| compound from example | serum cholesterol | serum triglycerides | serum cholesterol | serum triglycerides | serum cholesterol | serum triglycerides |
| Clofibrate | −14/−7 | −22/−15 | | | | |

TABLE 2

% change of carbohydrate induced hypertriglyceridemia in male rats after a 3-days peroral pretreatment with the indicated doses

| | 100 mg/kg/day | | 30 mg/kg/day | |
|---|---|---|---|---|
| compound from Example | serum cholesterol | serum triglycerides | serum cholesterol | serum triglycerides |
| 7 | | −37 | | |
| 10 | | | −12 | −14 |
| Clofibrate | | −34 | | |

The following Examples illustrate the invention:

1. 5-(p-Chlorophenyl)-2,3,4,9b-tetrahydro-1H-indeno [1,2-b]-pyridine-2-one a. 0.05 mole of benzoyl-butyric acid nitrile and 0.05 mole of 4-chlorobenzaldehyde were reacted in a mixture of 25 ml of 85% phosphoric acid and 25 g of phosphorus pentoxide for 90 minutes at 80° C. The reaction mixture was poured onto 500 ml of water, the raw product was filtered off with suction and recrystallized from ethanol. M.p. 256°–258° C.

b. 0.05 mole of 6-phenyl-3,4-dihydro-pyridine-2-one were heated with 0.05 moles of 4-chlorobenzaldehyde for 90 minutes in a mixture of 25 ml of 85% phosphoric acid and 25 g of phosphorus pentoxide to 80° C. The whole was poured into water, filtered off with suction and the product was recrystallized from ethanol. M.p. 257°–258° C.

2. 5-(p-nitrophenyl)-2,3,4,9b-tetrahydro-1H-indeno [1,2-b]-pyridine-2-one

Obtained in a manner analogous to 1 a) from γ-benzoyl-butyric acid nitrile and 4-nitrobenzaldehyde. M.p. 287° C (decomposition).

3. 5-(p-methoxyphenyl)-2,3,4,9b-tetrahydro-1H-indeno [1,2-b]-pyridine-2-one

Obtained in a manner analogous to 1 a) from γ-benzoyl-butyric acid nitrile and 4-methoxy-benzaldehyde. M.p. 196°–198° C.

4. 5-Phenyl-2,3,4,9b-tetrahydro-1H-indeno-[1,2-b]-pyridine-2-one a. Obtained in a manner analogous to 1 a) from γ-benzoylbutyric acid nitrile and benzaldehyde. M.p. 234°–235° C.

b. 5 Millimoles of 6-phenyl-5-[α-(6-phenyl-3,4-dihydropyridine-2-one-5-yl)-benzyl]-3,4-pyridine-2-one were heated for 3 hours to 80° C in a mixture of 10 ml of 85% phosphoric acid and 10 g of phosphorus pentoxide. The reaction mixture was combined with water, filtered off with suction and the product was recrystallized from ethanol. M.p. 234°–235° C.

5. 7-Methoxy-5-p-chlorophenyl-2,3,4,9b-tetrahydro-1H-indeno-[1,2-b]-pyridine-2-one Obtained analogous to 1 a) from γ-4-methoxy-benzoylbutyric acid nitrile and 4-chlorobenzaldehyde. M.p. 243°–246° C.

6. 4a(S,R); 5(S,R); 9b(S,R)-5-p-aminophenyl-2,3,4,4a,5,9b-hexahydro-1H-indeno [1,2-b]-pyridine-2-one-hydrochloride 0.2 mole of 5-p-nitrophenyl-2,3,4,9b-tetrahydro-1H-indeno [1,2-b]-pyridine-2-one were dissolved in a mixture of 1.5 liters of dimethylformamide and 1.5 liters of methanol and hydrogenated at 50° C and 50 atmospheres gauge with Raney nickel. The reaction time was 20 hours. The mixture was filtered with suction, the residue was heated with dimethylformamide, filtered and the reaction product was filtered off with suction after crystallization. M.p. 258°–262° C (hydrochloride).

7. 4a(S,R); 5(S,R); 9b(S,R)-5-phenyl-2,3,4,4a,5,9b-hexahydro-1H-indeno [1,2-b]-pyridine-2-one Obtained in a manner analogous to 6 from 5-phenyl-2,3,4,9b-tetrahydro-1H-indeno [1,2-b]-pyridine-2-one. M.p. 213°–216° C.

8. 5-Phenyl-2,3,4,9b-tetrahydro-1H-indeno [1,2-b] pyridine-2-thione a. 20 Millimoles of 5-phenyl-2,3,4,9b-tetrahydro-1H-indeno [1,2-b] pyridine-2-one were introduced into a suspension of 8 millimoles of phosphorus pentasulfide and 32 millimoles of calcium oxide in 50 ml of toluene, while stirring, and heated for 15 hours under reflux. The hot toluene solution was decanted from the residue through a filter and the resin was extracted twice with 50 ml portions of benzene. The combined organic solutions were concentrated under reduced pressure and the remaining oil was recrystallized from ethanol. M.p. 206°–208° C.

b. 20 Millimoles of 5-phenyl-2,3,4,9b-tetrahydro-1H-indeno [1,2-b]-pyridine-2-one were introduced into a suspension of 20 millimoles of phosphorus pentachloride in 20 ml of toluene and subsequently boiled for 3 hours under reflux. Then, $H_2S$ was introduced at room temperature until the evolution of HCl had terminated. The solvent was removed under reduced pressure and the residue was recrystallized from ethanol. M.p. 206°–208°C.

c. 90 Millimoles of 5-phenyl-2,3,4,9b-tetrahydro-1H-indeno [1,2-b] pyridine-2-one were dissolved in 35 ml of pyridine and 40 mmoles of phosphorus pentasulfide were added, while stirring. The solution was heated for 4 hours under reflux and after cooling poured into 400 ml of water. The pH-value was adjusted to 8 to 8.5 by means of 10% potassium hydroxide solution and the whole was stirred for 4 hours. After filtration with suc-

9. 4a(S,R); 5(S,R); 9b(S,R)-5-phenyl-2,3,4,4a,5,9b-hexahydro-1H-indeno [1,2-b]-pyridine-2-one Obtained in a manner analogous to (8a) from 4a(S,R); 5(S,R); 9b(S,R)-5-phenyl-2,3,4,4a,5,9b-hexahydro-1H-indeno [1,2-b] pyridine-2-one, M.p. 235°–237° C.

10. 5-p-Chlorophenyl-2,3,4,9b-tetrahydro-1H-indeno [1,2-b] pyridine-2-thione Obtained in a manner analogous to 8a) from 5-p-chlorophenyl-2,3,4,9b-tetrahydro-1H-indeno [1,2-b]-pyridine-2-one. M.p. 193°–195° C.

11. 4a(S,R); 5(S,R); 9b(S,R)-5-p-chlorophenyl-2,3,4,4a,9b-hexahydro-1H-indeno [1,2-b] pyridine-2-one Obtained in a manner analogous to 6 from 5-p-chlorophenyl-2,3,4,9b-tetrahydro-1H-indeno [1,2-b]-pyridine-2-one. M.p. 236°–238° C.

12. 7,8-Dimethoxy-5-phenyl-2,3,4,9b-tetrahydro-1H-indeno [1,2-b] pyridine-2-one Obtained in a manner analogous to 1 a) from γ-3,4-dimethoxybenzoylbutyric acid nitrile and benzaldehyde. M.P. 240°–242° C.

13. 4a(S,R); 5(S,R); 9b(S,R)-7,8-dimethoxy-5-phenyl-2,3,4,4a,5,9b-hexahydro-1H-indeno [1,2-b] pyridine-2-one Obtained in a manner analogous to 6 from 7,8-dimethoxy-5-phenyl-2,3,4,9b-tetrahydro-1H-indeno [1,2-b] pyridine-2-one. M.p. 259°–260° C.

14. 4a(S,R); 5(S,R); 9b(S,R)-7,8-dimethoxy-5-p-chlorophenyl-2,3,4,4a,5,9b-hexahydro-1H-indeno [1,2-b]-pyridine-2-one a. 7,8-Dimethoxy-5-p-chlorophenyl-2,3,4,9b-tetrahydro-1H-indeno [1,2-b]-pyridine-2-one, prepared in a manner analogous to 1 (a) from γ-3,4-dimethoxybenzoylbutyric acid nitrile and 4-chlorobenzaldehyde. M.p. 274°–276° C.

b. 4a(R,S); 5(S,R); 9b(S,R)-7,8-dimethoxy-5-p-chlorophenyl-2,3,4,4a,5,9b-hexahydro-1H-indeno [1,2-b]-pyridine-2-one, prepared in a manner analogous to 6 from 7,8-dimethoxy-5-p-chlorophenyl-2,3,4,9b-tetrahydro-1H-indeno [1,2-b]-pyridine-2-one. M.p. 305°–307° C.

15. 7-Methoxy-5-p-chlorophenyl-2,3,4,9b-tetrahydro-1H-indeno-[1,2-b]-pyridine-2-thione Prepared in a manner analogous to 8 a) from 7-methoxy-5-p-chlorophenyl--2,3,4,9b-tetrahydro-1H-indeno [1,2-b]-pyridine-2-one. M.p. 202°–203° C.

16. 5-(4'-Pyridyl)-2,3,4,9b-tetrahydro-1H-indeno [1,2-b]-pyridine-2-one

Obtained in a manner analogous to 1a) from γ-benzoyl-butyric acid nitrile and pyridine-4-aldehyde. M.p. 226°–229° C.

17. 7-Chloro-5-phenyl-2,3,4,9b-tetrahydro-1H-indeno [1,2-b]-pyridine-2-one

Obtained in a manner analogous to 1 a) from γ-4-chlorobenzoylbutyric acid nitrile and benzaldehyde. M.p. 258°–262° C.

18. 4a(S,R); 5(S,R); 9b(S,R)-7-chloro-5-phenyl-2,3,4,4a,5,9b-hexahydro-1H-indeno [1,2-b]-pyridine-2-one Obtained in a manner analogous to 6 from 7-chloro-5-phenyl-2,3,4,9b-tetrahydro-1H-indeno [1,2-b]-pyridine-2-one. M.p. 234°–238° C.

19. 4a(S,R); 5(S,R); 9b(S,R)-7,8-dimethoxy-5-phenyl-2,3,4,4a,5,9b-hexahydro-1H-indeno [1,2-b]-pyridine-2-thione Obtained in a manner analogous to 8(a) from 4a(S,R); 5 (S,R); 9b(S,R)-7,8-dimethoxy-5-phenyl-2,3,4,4a,5,9b-hexahydro-1H-indeno [1,2-b]-pyridine-2-one. M.p. 290°–293° C.

20. 4a(S,R); 5(S,R); 9b(S,R)-5-phenyl-2,3,4,4a,5,9b-hexahydro-1H-indeno [1,2-b]-pyridine-2-one 5 g of 4a(S,R); 5(S,R); 9b(S,R)-5-phenyl-2,3,4,4a,5,9b-hexahydro-1H-indeno [1,2-b] pyridine-2-one and 25 g of KOH were boiled in 25 ml of butanol for 14 hours under reflux. The reaction mixture was poured on water, extracted with ether, adjusted to pH 4 with dilute acid and filtered off with suction. (After recrystallization from ethanol, the acid was found to melt at 148°–150° C).

3 g of the amino-acid prepared as described above were boiled in 80 ml of benzene with addition of catalytic amounts of p-toluene-sulfonic acid on a water separator until no water passed over. The benzene solution was washed once with a dilute bicarbonate solution, dried and concentrated under reduced pressure and the product was recrystallized from dimethylformamide. M.p. 150°–155° C.

We claim:
1. A partially-hydrogenated 1H-indeno-[1,2-b]-pyridine compound of the formula

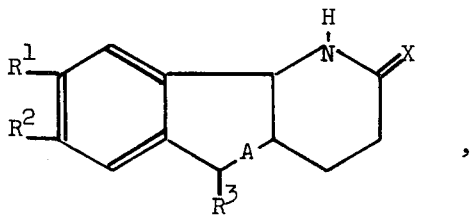

and physiologically tolerated salts thereof, wherein
$R^1$ and $R^2$, which are the same or different, are hydrogen, halogen, or alkoxy having 1–4 carbon atoms; $R^3$ is pyridyl, phenyl, or phenyl mono- or di-substituted by halogen, nitro, amino, or alkoxy having 1–4 carbon atoms; A is a single or double bond; and X is oxygen or sulfur.

2. 4a(S,R); 5(S,R); 9b(S,R)-5-phenyl-2,3,4,4a,5,9b-hexahydro-1H-indeno[1,2-b]-pyridine-2-one, as claimed in claim 1.

3. 4a(S,R); 5(S,R); 9b(S,R)-5-phenyl-2,3,4,4a,5,9b-hexahydro-1H-indeno[1,2-b]pyridine-2-thione, as claimed in claim 1.

4. 4a(S,R); 5(R,S); 9b(S,R)-5-phenyl-2,3,4,4a,5,9b-hexahydro-1H-indeno[1,2-b]pyridine-2-one, as claimed in claim 1.

5. 4a(S,R); 5(R,S); 9b(S,R)-5-phenyl-2,3,4,4a,5,9b-hexahydro-1H-indeno[1,2-b]pyridine-2-thione, as claimed in claim 1.

6. 4a(S,R); 5(S,R); 9b(S,R)-7-chloro-5-phenyl-2,3,4,4a,5,9b-hexahydro-1H-indeno[1,2-b]pyridine-2-one, as claimed in claim 1.

7. 4a(S,R); 5(R,S); 9b(S,R)-7-chloro-5-phenyl-2,3,4,4a,5,9b-hexahydro-1H-indeno[1,2-b]pyridine-2-one, as claimed in claim 1.

8. 5-p-chlorophenyl-2,3,4,9b-tetrahydro-1H-indeno[1,2-b]-pyridine-2-thione, as claimed in claim 1.

9. 7-chloro-5-phenyl-2,3,4,9b-tetrahydro-1H-indeno[1,2-b]-pyridine-2-one, as claimed in claim 1.

* * * * *